(12) United States Patent
Rührnschopf

(10) Patent No.: US 7,308,072 B2
(45) Date of Patent: Dec. 11, 2007

(54) DEVICE AND METHOD FOR X-RAY SCATTER CORRECTION IN COMPUTER TOMOGRAPHY

(75) Inventor: Ernst-Peter Rührnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 183 days.

(21) Appl. No.: 11/154,727

(22) Filed: Jun. 16, 2005

(65) Prior Publication Data

US 2006/0008046 A1    Jan. 12, 2006

(30) Foreign Application Priority Data

Jun. 16, 2004    (DE) .................. 10 2004 029 009

(51) Int. Cl.
*G01N 23/083* (2006.01)
(52) U.S. Cl. .................. 378/7; 378/98.4; 378/98.12
(58) Field of Classification Search .............. 378/7, 378/98.4, 98.12
See application file for complete search history.

(56) References Cited

U.S. PATENT DOCUMENTS

| | | | | |
|---|---|---|---|---|
| 4,918,713 | A | * | 4/1990 | Honda .................. 378/98.4 |
| 5,666,391 | A | | 9/1997 | Ohnesorge et al. |
| 5,905,809 | A | * | 5/1999 | Timmer .................. 382/131 |
| 6,134,297 | A | * | 10/2000 | Chao .................. 378/98.12 |
| 6,256,367 | B1 | * | 7/2001 | Vartanian .................. 378/7 |
| 6,618,466 | B1 | | 9/2003 | Ning |
| 6,639,964 | B2 | * | 10/2003 | Schneider et al. .............. 378/7 |
| 7,145,980 | B2 | * | 12/2006 | Sakaguchi et al. .............. 378/7 |

OTHER PUBLICATIONS

Ruola Ning, Xiangyang Tang, and D.L. Conover, "X-ray Scatter Suppression Algorithm For Cone Beam Volume CT", Proceedings of SPIE 2002, pp. 774-781, vol. 4682.
L. Spies, M. Ebert, B.A. Groh, B.M. Hesse and T. Bortfeld, "Correction of Scatter in Megavoltage Cone-beam CT", Physics in Medicine and Biology, 2001, pp. 821-833, vol. 46, IOP Publishing Ltd, UK.
Karl Wiesent, K. Barth, N. Navab, P. Durlak, T. Brunner, O. Schuetz and W. Seissler, "Enhanced 3-D-Reconstruction Algorithm for C-Arm Systems Suitable for Interventional Procedures", IEEE Transactions on Medical Imaging, No. 5, May 2000, pp. 391-403, vol. 19.
Vibeke N. Hansen, William Swindell and Philip M. Evans, "Extraction of Primary Signal From EPIDs Using Only Forward Convolution", Medical Physics, Sep. 1997, pp. 1477-1484, vol. 24, No. 9.
L.A. Feldkamp, L.C. Davis and J.W. Kress, "Practical Cone-Beam Algorithm", J. Opt. Soc. Am. A, Jun. 1984, pp. 612-619, vol. 1, No. 6.
Willi Kalender, "Monte Carlo Calculations of X-Ray Scatter Data for Diagnostic Radiology", Physics in Medicine and Biology, 1981, pp. 835-849, vol. 26, No. 5.

* cited by examiner

*Primary Examiner*—Edward J. Glick
*Assistant Examiner*—Thomas R. Artman

(57) ABSTRACT

A device (1) for computer tomography, which is set up for x-ray scatter correction, features an evaluation unit (17) which evaluates values stored as a table in a data memory for x-ray scatter correction, which have been determined in advance with the aid of a Monte Carlo simulation which take account of interactions of the photons with the object (2) to be investigated.

10 Claims, 6 Drawing Sheets

DEVICE AND METHOD FOR X-RAY SCATTER CORRECTION IN COMPUTER TOMOGRAPHY

CROSS REFERENCE TO RELATED APPLICATIONS

This application claims priority to the German application No. 10 2004 029 009.1, filed Jun. 16, 2004 which is incorporated by reference herein in its entirety.

FIELD OF INVENTION

The invention relates to a device for computer tomography with a radiographic source, a detector and an evaluation unit arranged after the detector which uses the projection images supplied by the detector and taken from a variety of projection directions to determine scattering information, and on the basis of the scattering information, corrects the x-ray scatter component in the projection images.

The invention further relates to a method with x-ray scatter correction for computer tomography as well as to a method for obtaining scattering information.

BACKGROUND OF INVENTION

A device and a method of this type with scattering correction are known from U.S. Pat. No. 5,666,391 A. The known device and the known method allow x-ray scatter to be corrected within the framework of computer tomography.

Computer Tomography (=CT) is a well-known method with which the three-dimensional reconstruction of the tissue density distribution, or to put it more precisely of the linear coefficient of attenuation of x-rays, of the inside of the body is possible with high spatial resolution and great quantitative accuracy of density resolution. The spatial resolution is typically <=1 mm and the density resolution typically amounts to a few Hounsfield Units (1 HU=$\frac{1}{1000}$ of the density of water).

With two-dimensional detectors with a typical size of around 40 cm×40 cm such as for example x-ray image amplifiers or Flat-Panel Detectors (=FPD), It is possible, with just a single half rotation, which extends over more than 180 degrees and the cone angle, to record and to reconstruct an image of a large volume area, (=Conebeam CT=CBCT).

SUMMARY OF INVENTION

A serious problem is however the x-ray scatter generated in the object or patient under examination, the intensity of which can reach and in some cases even exceed the order of magnitude of the unscattered, direct primary radiation. One of the consequences is a significant deterioration of the quantitative tissue density reconstruction, another is that artifacts are produced. Errors of several hundred 100 HU can thus occur and dark shadows or bar artifacts between strongly absorbent structures can lead to incorrect diagnoses.

It is thus of advantage for the x-ray scatter to be able to be effectively suppressed.

In conventional CT with single-row or multirow detectors the x-ray scatter is effectively suppressed with the aid of collimators: on the one hand by diaphragms which restrict the solid angle of the radiation to the solid angle under which a single-row detector or a multi-row detector appears as seen from the radiographic source (=axial collimation, meaning that the angle is restricted in the axis of rotation), on the other hand by encapsulation or by lateral collimator panels between adjacent detector elements (=lateral collimation).

The development of a specific two-dimensional collimator which matches the flat-panel detector with micrometer accuracy and simultaneously would have to be focused on the focal point of the x-ray tube, is very difficult and would, even if it were technically possible, be extraordinarily expensive.

In the publication R.NING, X.TANG, D.L.CONOVER: X-ray scatter suppression algorithm for cone beam volume CT. in: Proc., Vol. 4682, 2002, pages 774-781 the proposal was made to measure and correct the x-ray scatter in a few directions of projection. To measure the x-ray scatter a device must be available with which a beamstop carrier plate can be moved near to the patient into the beam path between x-ray source and patient. The additional measurement procedure required is however not acceptable in the normal clinical sequence of operations.

Computation corrections which are efficient as regards accuracy and outlay are not yet known for CBCT. U.S. Pat. No. 5,666,391 A does however propose a computational x-ray scatter correction for fourth-generation CT devices with a fixed ring of detector elements of one or more rows, in which an effective lateral collimation is basically not possible and its general application to flat panel detectors.

A basic disadvantage of the method known from U.S. Pat. No. 5,666,391 and of the known device relates to accuracy and lies in the fact that projection data is corrected directly without recourse to the reconstructed image (volume) and the information available within it about the scatter object is not used in the correction.

Furthermore the use of Monte Carlo methods to simulate the spread of x-rays in radiography is known from W. KALENDER: Monte Carlo calculations of x-ray scatter data for diagnostics radiology. in: Phys. Med. Biol., 1981, Vol. 26, No. 5, pages 835-849.

An object of the invention is to specify a device and a method with which an improved method of x-ray scatter correction as regards accuracy compared to the prior art can be performed.

This object is achieved by the claims.

The device for computer tomography has a radiographic source, a detector and an evaluation unit arranged after the detector. On the basis of the projection images, the evaluation unit determines a three-dimensional object model differentiated in accordance with scatter characteristics and, depending on the object model, reads out from a data memory scatter information of which the parameters depend on the object model. The scatter information is in particular scatter distributions determined in advance using Monte Carlo simulations in which multiple interactions of the photons with the object to be examined are taken into account.

The solution proposed here has the following advantages: No additional measurement is needed. Furthermore no mechanical modification is necessary and no additional devices are needed for the CBCT scanner. The purely computational correction uses information from the reconstructed volume and by virtue of this feedback is more accurate than methods which only operate directly on the projection data without recourse to the image volume. Finally the correction algorithm can be reduced to a fraction of the computation requirements for a standard reconstruction without correction.

In a preferred embodiment the scatter information is scatter distributions which describe the scatter-induced distribution of the radiation emitted from the radiographic source and directed to a specific detector element on adjacent detector elements.

The result of using this type of scatter distribution is that during the actual processing of the projection data and the subsequent volume reconstruction extensive calculations are no longer required to obtain the scatter information required for correction. Instead the scatter information is obtained by assignment to sufficiently finely differentiated scatter categories—if necessary by means of additional Interpolation—which is already present through advance calculation for corresponding data acceptance conditions and scatter object configurations.

With a further preferred form of embodiment the evaluation unit determines the x-ray scatter proportion in an area of the projection image in which the evaluation unit computes and adds the scatter radiation contributions of the surrounding image areas. The individual x-ray scatter contributions are in this case a function of the non-scattered x-ray components assigned to the adjacent image areas in each case. The distribution of the non-scattered x-ray components over the projection image is finally produced as a solution to the equation T=P+S (P), with T being the entire measured x-ray distribution, P the distribution of the non-scattered x-ray components and S the distribution of the x-ray scatter components. The latter depends on the distribution of the sought distribution of the unscattered x-ray components.

In this embodiment of the x-ray scatter correction undertaken by the evaluation unit the distribution of the non-scattered x-ray components sought is produced as a solution to an implicit equation. These types of equation can be solved numerically by iteration.

With a further preferred embodiment a number of elementary image elements of the detector are assembled into shared image areas and the scatter correction computed for the individual image areas. This offers the advantage of being able to reduce the computing overhead for scatter correction.

In a further preferred embodiment the evaluation unit segments the object model of the object to be examined in that, depending on scatter parameters of the material covered by the volume element, the evaluation unit assigns the volume element to a scatter category from a set of scatter categories determined in advance.

This measure serves to simplify the setting of parameters for the scatter information, since in this case the scatter information only has to be calculated for the predetermined discrete scatter categories.

To keep the calculation of the scatter correction simple, the object model used to calculate the scatter correction exhibits a low discrete local resolution on the object model created after the evaluation unit has run the scatter correction.

Since the x-ray scatter distribution has a low-frequency Fourier spectrum, this measure allows the computing effort for x-ray scatter correction to be reduced.

The x-ray scatter correction itself can be performed in a different way. On the one hand it is possible, for the evaluation unit to perform an x-ray scatter correction on the projection images and with the aid of x-ray scatter corrected projection images to create a volume image with full local resolution in each case. The procedure is a good idea if the x-ray scatter distribution contains higher-frequency local frequency components On the other hand however it is also possible, on the basis of the distribution of the uncorrected radiation components, to create a correction volume image of lower local resolution, which is used for correction of a volume image of high local resolution which has been created on the basis of the uncorrected projection images. The latter procedure reduces the computing effort, since the volume image does not have to be created multiple times with full resolution.

BRIEF DESCRIPTION OF THE DRAWINGS

Further details and advantages of the invention can be taken from the description below, in which the exemplary embodiments of the invention are described in detail on the basis of the enclosed drawing. The figures show.

DETAILED DESCRIPTION OF INVENTION

Figure 1:
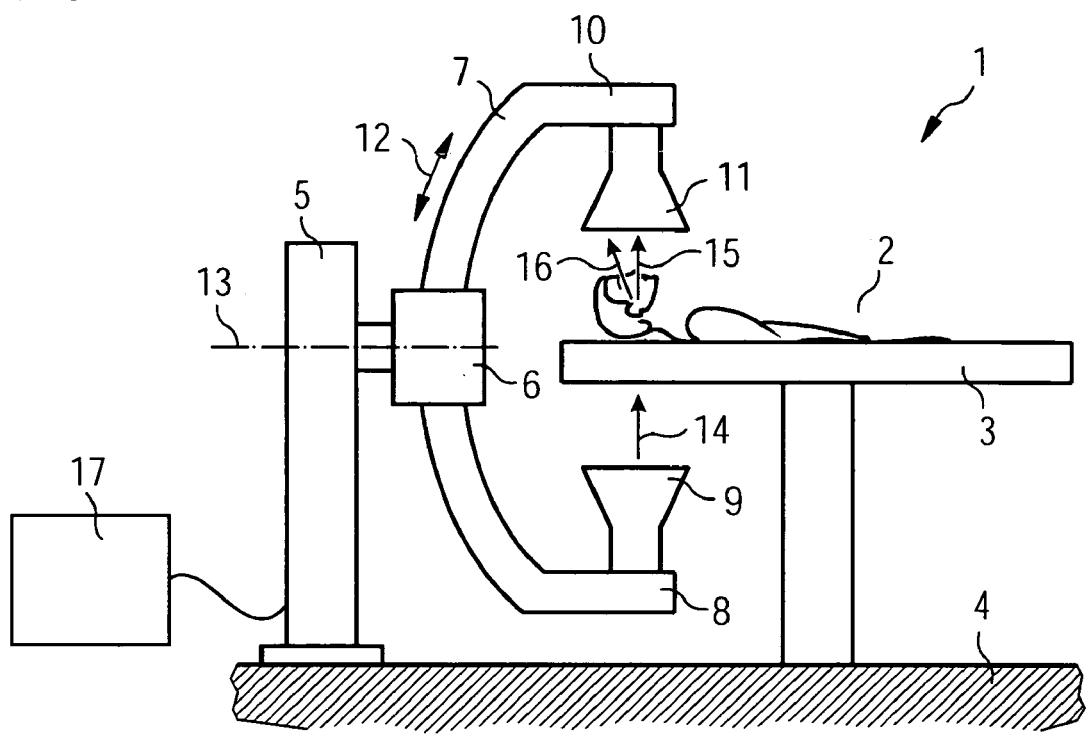
FIG. 1 a side view of a computer tomography unit.

FIG. 1 shows a computer tomography device 1 which is used to examine a patient 2. The patient 2 is on a support bed 3 which stands on a floor 4. On the floor 4 there is also a stand 5 with a holder 6 for a C-arm 7 which has a radiographic source 9 on one of its ends 8 and on the other end 10 has a detector 11. The C-arm 7 can be moved in the holder 6 in a circular direction 12. Furthermore the C-arm 7 can be swiveled around a pivot axis 13.

Further computer tomography devices not shown have floor-mounted C-arms or a combination of C-arms mounted on the floor 4 and on the ceiling. Other computer tomography devices feature an encircling frame (=CT-gantry), in which the X-ray tube is rigidly connected to the detector and with which this rotates around a pivot axis at high angular speed.

With the computer tomography unit 1 radiation 14 is emitted from the radiographic source 9 which will also be referred to as source radiation 14 below. A component of the radiation 14 designated as primary radiation 15 passes through the patient 2 without changing its direction and reaches the detector 11. A further component of the radiation 14 designated as secondary radiation or scatter radiation 16 undergoes scattering at least once on its way from the radiographic source 9 to the detector 11 and is deflected from its original direction.

It should be pointed out that the term scattering is to be taken to mean any type of interaction between the radiation 14 and the material lying on the path between radiographic source 9 and detector 11, through which a change in the spread direction of the photons of the radiation 14 is brought about.

Through the secondary radiation 16 in a volume image which has been created on the basis of projection images recorded by the imaging detector 11, artifacts can be produced which can lead to errors in diagnosis. To this end scatter correction is performed in an evaluation unit 17 connected to the computer tomography device 1, for which the execution sequence is sketched out in FIG. 2.

Figure 2:
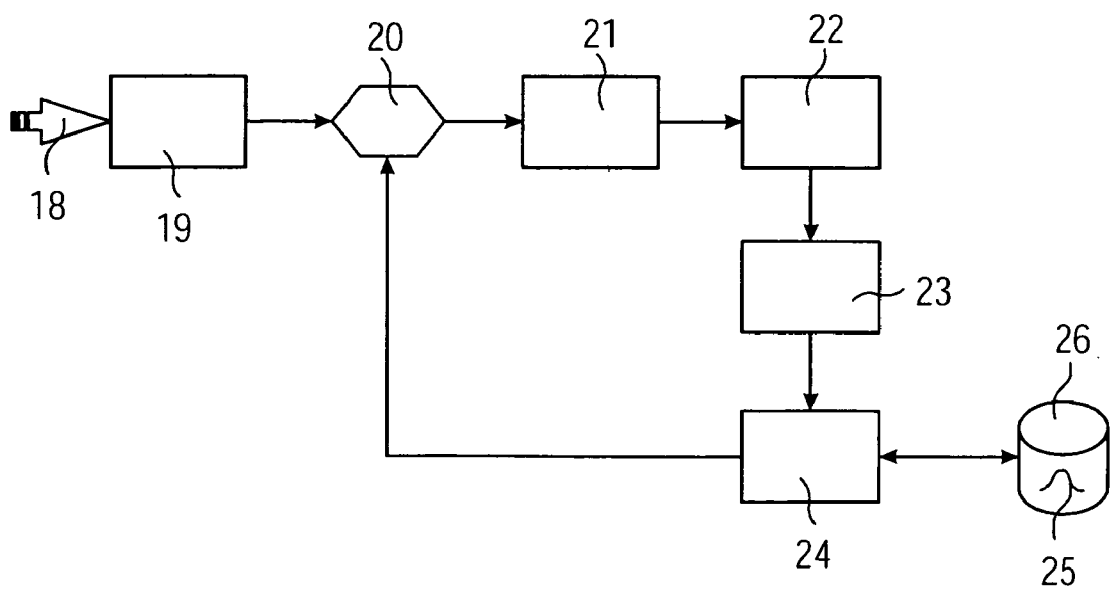
FIG. 2 an overview diagram of the sequence of the scatter correction.

In accordance with FIG. 2, as the C-arm 7 rotates around the pivot axis 13 or with a movement of the C-arm 7 in a circular direction a data recording 18 is undertaken, during which a series of projection images 19 are recorded from different projection directions. To avoid artifacts the projection images 19 must be subjected to a scatter correction 20. After an image reconstruction 21 a three-dimensional volume image 22 largely free of artifacts of the object to be examined is produced.

The data for the scatter correction 20 is obtained as follows: First the required scatter correction is estimated or the projection images 19 are included in their uncorrected state for image reconstruction 21. The initially uncorrected volume image 22 is then converted into a scatter model 23 which forms the basis for image data calculation 24. The image data calculation 24 in this case uses what are known as scatter beam spread functions 25 (=SBF), which are stored in a measurement data memory 26. The projection images 19 are then subjected to scatter correction 20 with the aid of the scatter data. After a renewed image reconstruction 21 a new scatter-corrected volume image is created 22.

The method outlined in FIG. 2 will now be explained in detail.

The method described in detail below is based on the concept of a Scatter-Beam-Spread-Function=SBF 25 which is also inhomogeneous under some circumstances. The SBF 25 describes the spatial intensity distribution of the scatter radiation or the secondary radiation 16 on the flat-panel detector 11 for a thin x-ray beam 14 which passes through the scatter object (=volume of the patient 2).

Figure 3:
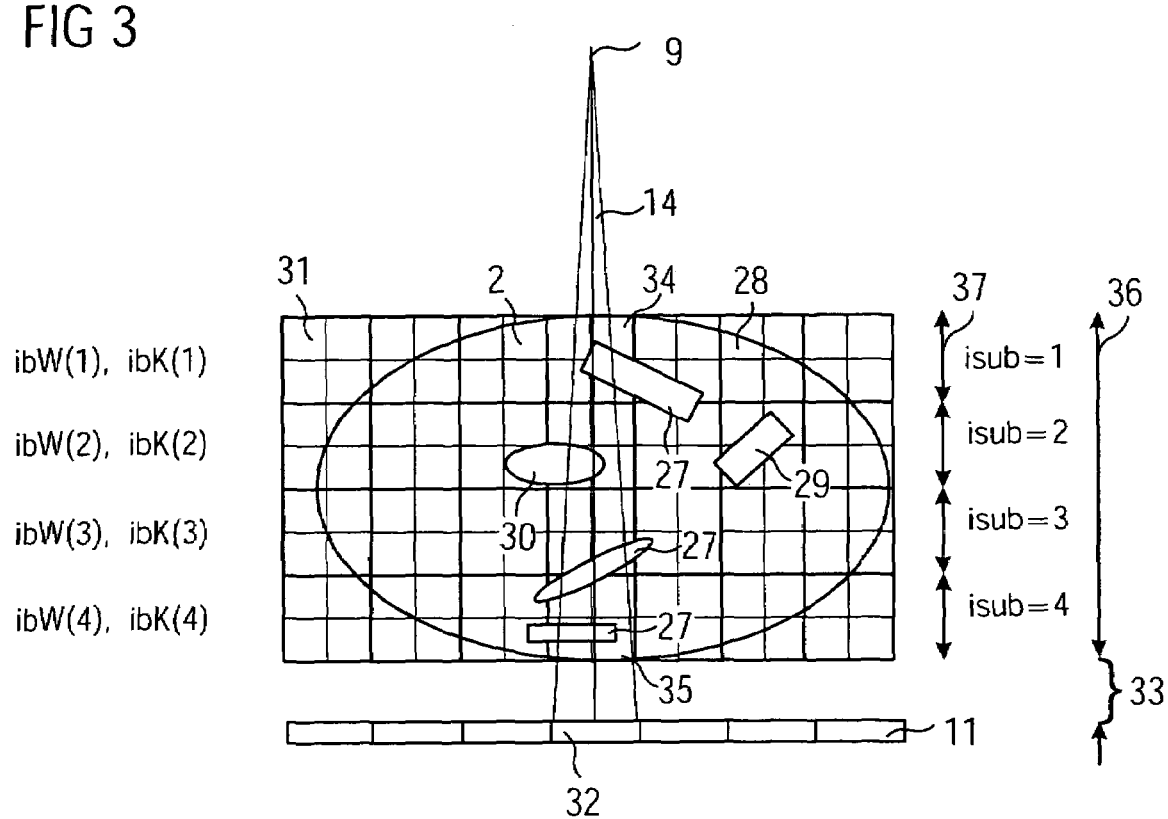
FIG. 3 a presentation of a segmented reprojection for an object to be examined inhomogeneously.

The SBF 25 depends on the recording parameters and on object parameters. Typical recording parameters are: Tube voltage, pre-filtering, air gap, SID (source—Image distance), collimation (detector inclusion), anti-scatter grid (or not). The object parameter is the (to be reconstructed) spatial distribution (of the attenuation coefficient) of the tissue in the patient 2. The SBF 25 depends especially on the generally inhomogeneous distribution in accordance with FIG. 3 of the tissue along the rays of the x-ray radiation 14, with it essentially being a matter of the different proportions of the bone tissue 27 or at least bone-type substance and soft tissue 28.

(1) The requirement is for the SBFs 25 to be available for the most important recording and object parameters which occur, meaning that a table (=SBF atlas) created in advance is available with the aid of which it is possible, for the specific given recording conditions, to determine the associated SBF 25 sufficiently accurately for each inhomogeneous distribution of bone tissue 27 and soft tissue 28. This might be done by interpolation in the SBF atlas or by semi-empirical transformations for parameters, on which the SBF is only slightly dependent or for which functional dependencies are known. The latter is for example the case in relation to the SID.

(2) A segmentation algorithm is required, with which—using something like a threshold criterion—a separate presentation of the bone volume and of the soft tissue volume can be created from the three-dimensional object volume. A further differentiation, for example between metal 29 or air 30, is basically possible.

(3) A reprojection algorithm, with the aid of which the length of an x-ray beam 14 corresponding to the recording geometry of the individual contributions of the bone tissue 27 and of the soft tissue 28 to the attenuation can be computed and summed in a localized way.

(4) A reconstruction algorithm in order to perform an object volume reconstruction from cone beam projection data, for example a method based on filtered back projections. Such methods are described for example in L. A. FELDKAMP, L. C. DAVIS, J. W. KRESS: Practical cone-beam algorithm. in: J. Opt. Soc. Amer. A, Vol. 6, 1984, pages 612-619 and in K. WIESENT, K. BARTH, N. NAVAB u. a.: Enhanced 3-D-Reconstruction Algorithm for C-Arm system Suitable for Interventional Procedures. in: IEEE Trans. Med. Imaging, Vol. 19, No. 5, May 2000, pages 391-403.

(5) It is required that an object volume reconstruction from the uncorrected or only roughly corrected projection images 19 (=CBCT projection data) is present.

Description of the Individual Processing Steps

The processing is undertaken at different levels in a number of nested loops, in ascending order: (I) the level of the object volume, (II), (II') the level of the CT projections and (III) the level of the individual beam or individual detector areas.

(I) Preparation of the Object Volume (1) Decimation of the voxel discretization by binning.

Binning (=downsampling) should be understood as the grouping together of nbin_vol voxels 31 (=volume element) in each dimension in each case. With this binning the number of voxels 31 to be processed is very drastically reduced for the segmentation and the reprojection. For example with binning of a voxel size of 0.4 mm to 1 cm a decimation of the number of voxels by a factor >10000 is achieved.

Accordingly a decimation of the discretization of the pixel 32 (=detector elements) of the detector 11 is undertaken by binning of each nbin_det detector pixels 32 of the detector For example for binning of a pixel size of 0.4 mm to 1 cm a decimation of the number of pixels by a factor of 625 is achieved.

(2) Segmentation of the volume into soft tissue and bone components.

In the simplest for of segmentation the voxels 31 are classified with the aid of a gray value threshold Gschw. A gray value>=Gschw means bone tissue 27. A gray value<=Gschw means soft tissue 28. This allows separate object volumes to be created: a pure bone volume a pure soft tissue volume.

(II) for each CT Projection:

(3) Pre-analysis of the still uncorrected or only very coarsely corrected volume and determination of the air gap iairgap.

The air gap 33 is the gap between the detector 11 and the object to be examined. The air gap 33 has a not-insignificant effect on the intensity of the x-ray scatter since only the x-ray scatter proportion which is directed to the detector 11 reaches the detector 11. As the gap between detector 11 and the object to be examined increases, the intensity of the x-ray scatter thus reduces.

(4) Segmented reprojection:

Reprojection, also called forwards projection, is the computer simulation of the passage of a beam of x-ray radiation 14 from the focal point of the radiographic source 9 through the object volume to the detector 11.

Beam in this context should be taken to mean a conical beam of x-ray radiation 14 which is directed to a specific detector pixel with each cone beam being represented by a ray iray in the sense of geometrical optics The term segmented reprojection is intended to express that the reprojection is applied to the segmented object volume for bone tissue 27 and soft tissue 28 and in addition that the ray of the x-ray radiation is divided up into a number of segments on its way through the object volume. This will be explained in greater detail below.

The segmented reprojection is executed for each CT projection direction iphi (0 to <360 degrees) and for each detector pixel 32 (after the binning), with the detector pixel 32 being identified by an index iray which designates the associated ray of the x-ray radiation 14. The segmented reprojection includes the following operations:

(III) for Each Detector Pixel iray, that is for Each Ray of the X-ray Radiation 14 Between Radiographic Source 9 and Detector Pixel 32:

i. Determination of an entry voxel 34 and of an exit voxel 35 in the object volume, that is the location of the entry and the exit of the ray iray on the surface of the patient 2, and thereby the ray length 36 in the object: irayleng.

ii. Subdivision of the ray length 36 into iray_sub subsections 37. The subdivision is to be adapted to the discretization of the SBF atlas (see below).

iii. Reprojection through the segmented bone and soft tissue volume, so that for each subsection i=1 . . . iray_sub the ray path length irayleng of the relevant (logarithmic) attenuation contribution of bone and soft tissue substance ibK(i) and ibW (i) is determined. The attenuation contributions are defined here as:

Sum of the products ray length in voxels*linear attenuation coefficient

The latter is produced from the gray value and the material, which can be either bone tissue 27 or soft tissue 28. Thus for each detector pixel iray a ray configuration consisting of a number of components f (=a vector) is computed:

$$f(iray, iphi) = (iairgap, irayleng, ((ibW(i), ibK(i)), i=1 \ldots iray\_sub, \ldots) \quad (eq. 1)$$

This means that the attenuation components along the length of the ray of the x-ray radiation 14 are described by the object volume. The ray configuration f is naturally also dependent on the energy spectrum, especially tube voltage selected, the filter used and further parameters. These are specific recording parameters but remain constant during data acquisition.

Lookup in the SBF atlas.

The creation of the SBF atlas will be described below in greater detail.

The lookup in the SBF atlas is undertaken for each ray iray.

For each ray iray (=each detector pixel 32) the (standardized) x-ray scatter intensity distributions or x-ray scatter spread functions 25 are available in the SBF atlas depending on a multiplicity of different scatter categories f':

$$SBF(f') = SBF(airgap, rayleng, ((bW(k), bK(k)), k=1 \ldots kray\_sub), spectrum, \ldots) \quad (eq. 2)$$

An SBF 25 is a two-dimensional function or a two-dimensional field of the row coordinates and column coordinates on the detector 11 and can be stored in relation to the binned detector pixel index units or also in finer discretization. Each SBF 25 is concentrated around a center, the relevant ray of the x-ray radiation 14 or the relevant detector pixel 32 with the coordinates (0,0), and drops sharply with the distance from the center of the ray. The distance from the center in both coordinate directions is identified by a pair of indexes (jx, jy) in which case for simplicity's sake we will use binned detector pixel units below. The SBF 25 is a type of point or line image function, where "point" or "line" is to be replaced by "ray"

The different notation in (Eq. 1) and (Eq. 2) should be noted. This is intended to emphasize that the SBF atlas has been created for specific discretizations of ray configuration f' which have been designated as scatter categories. The discretization of the parameters of the individual scatter categories does not generally tally with the discretization of the ray configurations determined with reference to the object model f. As a rule the specific ray configuration f in (Eq. 1) is thus not contained in the SBF atlas, so that SBF(f) must be obtained by interpolation in the SBF atlas. To identify the interpolation we use the notation SBFI(f; (jx, jy)).

Thus, for each ray of the x-ray radiation 14 (each detector pixel 32) iray we obtain that SBF with which this ray iray (this detector pixel 32) contributes to the overall x-ray scatter intensity distribution over the detector surface. We refer to this contribution as dS:

$$dS(jx, jy; iray; iphi) = SBFI(f(iray, iphi); (jx, jy)) \quad (Eq. 3)$$

The contributions dS must now be integrated over all detector pixels 32. Consequently one returns to the level of the projection images 19:

(II') For each CT projection:

(5) Integration of x-ray scatter distribution over the (possibly binned) detector surface The SBFs 25 are scaled to the exponential attenuation=1 of the relevant ray of the x-ray radiation 14 (detector pixel 32). Exponential attenuation in this context is to be seen as the intensity of the primary radiation 15, which is related to the intensity of the source radiation 14 output by the radiographic source 9. Source radiation here is to be understood as that x-ray radiation 14 which would be measured without a patient 2.

Because of the scaling of the SBFs 25 measured for the summation of all contributions dS the contributions of the individual SBFs 25 must be multiplied by the actual exponential attenuation.

Since the CT projection data which is used for the CT reconstruction algorithms, is as a rule logarithmatized attenuations, the logarithmization must be set so that it can be reversed again. If p (iray, iphi) is the CT projection value for the x-ray radiation 14 iray in the reprojection iphi, then the associated (exponential) attenuation value is:

$$P(iray, iphi) = \exp(-p(iray, iphi)) \quad (Eq. 4).$$

It should be pointed out that P (iray, iphi) is related to the intensity $I_0$ of the source radiation 14 emitted by the radiographic source 9, which would be registered without attenuation in the detector pixel 32.

Each ray(index) iray can be identified by a row/column index pair(ix, iy) of a detector pixel 32. The index iray in (Eq. 3) and (Eq. 4) can thus be replaced by the equivalent index pair (ix, iy).

We nowretain a ray iray or a detector pixel (ix, iy), and observe all rays kray or detector pixels (kx, ky) in relation to their contribution to the overall x-ray scatter in (ix, iy).

The SBF 25 appended to the detector pixel (kx, ky) then contributes in accordance with (Eq. 3) as follows:

$$dS(jx, jy; kray; iphi) * P(kx, ky, iphi) \quad \text{(Eq. 5)}$$

with jx=ix−kx, jy=iy−ky at the point iray=(ix, iy).

With (Eq. 3) to (Eq. 5) for the x-ray scatter at location (ix, iy) iphi: is obtained in the projection $$S(ix, iy; iphi) = \sum_{kx}\left(\sum_{ky}((dS(ix-kx, iy-ky; kx, ky; iphi) * P(kx, ky, iphi))\right) \quad \text{(Eq. 6)}$$

This is true for any detector pixel (ix, iy) and thus (Eq. 6) describes the entire x-ray scatter distribution in the projection iphi.

The x-ray scatter distribution S is thus produced by a type of location-dependent folding of the primary radiation distribution P with the location-independent scatter contributions described by SBFs 25.

(6) Lowpass filtering and optional refinement (=upsampling) with interpolation

Because of the multiple scatter processes creating it in the body of the patient 2 the x-ray scatter distribution is relatively smooth and thus has a low-frequency Fourier spectrum. To eliminate any possible high-frequency error components induced by processing steps (1) to (6) a two-dimensional smoothing is to be recommended.

At this point various embodiments now emerge, which will be described in greater detail below in the context of a more detailed description of different embodiments. Here we are demonstrating the easiest-to-describe embodiment, but not the best embodiment as regards computing effort:

With this embodiment the decimation of the detector pixel number by refinement (=upsampling) and interpolation is reversed to the original fine pixel grid in which the (uncorrected) projection data is given.

Depending on embodiment variant the x-ray scatter correction described below is executed on the fine or on the coarsened d etector pixel grid.

(7) X-ray scatter correction

In connection with (Eq.4) no reference was made as to the type of projection values meant: In fact the data available is initially uncorrected, that is data based on measurement which includes the overlaying of the primary radiation 15 (direct, unscattered radiation) and the x-ray scatter or secondary radiation 16. We describe this overlaying with:

$$T = P + S$$

where the terms have the following meanings:
T Distribution if the total radiation (measured uncorrected projection images 19)
P Primary radiation distribution (initially unknown, but sought)
S Secondary radiation distribution (initially unknown but estimated with the proposed model).

This directly produces with (Eq. 6) a subtractive x-ray scatter correction:

$$P(ix, iy; iphi) = T(ix, iy; iphi) - S(ix, iy; iphi) \quad \text{(Eq. 7)}$$

to estimate the primary radiation distribution.

Another correction, which is recommended in cases of a relatively large proportion of secondary radiation 16 (S/T>=0.5 means that the intensity of the secondary radiation overpowers the intensity of the primary radiation 15) is multiplicative x-ray scatter correction:

$$P = T/(1+S/P) \quad \text{(Eq. 8)}$$

It should be noted that the corrections in (Eq. 7) or (Eq. 8) are only approximate and do not deliver identical results. For S/T<<1 (Eq. 8) goes over into (Eq. 7).

(8a) Internal iteration

In (Eq. 7) and (Eq. 8) the term S occurs on the right hand side for x-ray scatter distribution which is in its turn to be calculated by (Eq. 6). (Eq. 6) however is defined by means of the (unknown) primary radiation distribution P which in its turn occurs on the left hand side of (Eq. 7) and (Eq. 8) and is only to be calculated by one of these equations. P thus occurs both on the left hand side and also on the right hand side of (Eq. 7) and (Eq. 8). Such implicit equations are to be solved iteratively. For S in (Eq. 6) we write:

$$S = S(P)$$

(Eq. 7) then reads:

$$P = T - S(P)$$

The iteration algorithm runs for the subtractive procedure (Eq.7) as follows:

Start of iteration: $P^{(0)} = T$ (or a possibly better estimation)

Iteration step: $P^{(n+1)} = T - S(P^{(n)})$, n+1>0;

and for the multiplicative method (Eq. 8):

Start of iteration: $P^{(0)} = T$ (or a possibly better estimation)

Iteration step: $P^{(n+1)} = P^{(n)} * T/(P^{(n)} + S(P^{(n)}))$, n+1>0.

The iteration sequence is aborted if the result changes just slightly between step n and n+1. In a good many cases just one iteration step is sufficient (n=0; n+1=1).

(8) Cone beam volume reconstruction

The x-ray scatter corrected primary intensity data from (Eq.7) or (eq.8) or after internal iteration in accordance with section (8a) are logarithmized $$p(ix, iy; iphi) = -\log P(ix, iy; iphi), \quad \text{(Eq. 9)}$$

and a new object volume reconstruction is then performed from this corrected CBCT projection data.

It is to be expected that a significant improvement will be achieved compared to the first uncorrected reconstruction.

(9) External iteration:

A further improvement, if desired, can be achieved by repeating the processing steps (1) to (9).

Creating the SBF Atlas

The atlas of the Scatter-Beam-Spread-Functions=SBFs 25) comprises, as already described above in processing step (5), the (scaled) x-ray scatter intensity distributions depending on a plurality of scatter categories f^:

$$SBF(f^\wedge) = SBF(\text{airgap, rayleng}, ((bW(k), bK(k)), k=1 \ldots ksu\ b), \text{voltage}, \ldots) \quad \text{(Eq. 2)}$$

SBF (f^) also contains the dependency of the x-ray energy spectrum of the tube voltage voltage, of the pre-filtering, of radiation-sensitive detector material (for example scintillation crystal) and the dependency on whether an anti-scatter grid is used or not and if necessary which anti-scatter grid is used.

An explanation will now be given below with reference to Figure to explain how a single SBF 25 is obtained.

Initially the length of the air gap 33 (=airgap), voltage, pre-filtering, detector material and possibly further parameters are recorded.

Figure 4:
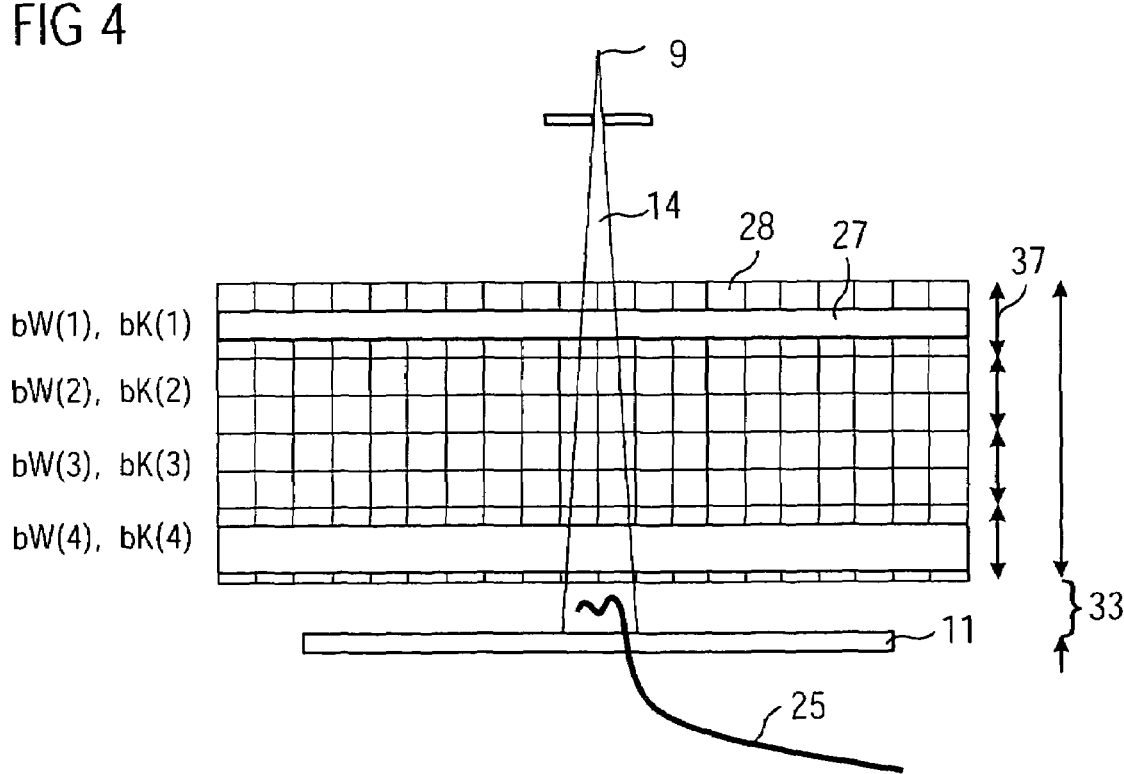
FIG. 4 a diagram of an object model used to calculate the x-ray scatter distribution function.

The ray length 36 of the x-ray radiation 14 in the object described by the parameter rayleng, for example 20 cm, is subdivided into a number ksub of subsections 37 of the same length raysub, for example 5 cm each. Then for each of the subsections 37 and the index k=1 . . . ksub a pair of mass occupancies (mass occupancy=length*density) for bone tissue bK(k) and soft tissue bW(k) is defined. A ray configuration of this type, which is actually three-dimensional, is shown in FIG. 4 in a two-dimensional cross-section.

It should be pointed out that with a sufficiently small subdivision into subsections 37 the SBF 25 practically no longer depends on the micro configuration of the distribution of bone tissue 27 and soft tissue 28 within the subsection k. Micro configuration in this case is understood to be the distribution of bone tissue 27 and soft tissue 28 in relation to the individual binned or unbinned voxels.

It should further be pointed out that the length of the subsections 27 does not necessarily have to correspond to the length of the binned or unbinned voxels 31. Instead it is worthwhile selecting the length of the subsections 37 in the order of magnitude of the average scatter path length which is as a rule greater than the length of the binned voxels. This will be explained in greater detail in connection with the discussion of the feasibility and the computing effort.

With the concept of the SBF 25 the distribution of the x-ray scatter created in the scatter body is of interest in the detector level if the (unscattered) ray of the x-ray radiation 14 is focused precisely on one detector pixel 32. If this is done consecutively for each detector pixel 32 and all associated SBFs 25 are summed, the overall x-ray scatter distribution is obtained.

An SBF is calculated for a configuration with the proven Monte Carlo method. Simplifications are made here but these can be very well justified:

Ignoring the divergence of the rays of the x-ray radiation 14 because of the cone beam geometry. Approximately parallel beam geometry is then assumed. The result achieved is that the SBF 25 remains the same for all detector pixels 32 if the ray configuration of the x-ray radiation 14 (=the material distribution along the ray of the x-ray radiation 14 does not change.

To improve the statistics with the Monte Carlo method and to reduce the computing effort, larger binned detector pixels 32 are used for calculation of the SBFs 25 (for example 1×1 cm$^2$ or 0.5×0.5 cm$^2$).

Within a subsection 37 of the ray configuration for each combination (bW(k), bK(k)) the distribution of bone tissue 27 and soft tissue 28 is homogenized. This means that both tissue types are distributed as a mixture event y spaced over the extent of the subsections 37.

Feasibility and Computing Effort for an SBF Atlas

It has already been pointed out that the SBFs 25 generally depend on a plurality of parameters. If one wished to discretize each parameter in accordance with the micro configuration of the ray in fine steps, millions of SBFs 25 would have to be calculated. This would be barely feasible since a Monte-Carlo calculation to obtain an SBF 25 with sufficient accuracy on of a modern workstation computer takes several minutes at least. Therefore a solution must be found which on the one hand can be executed with manageable computing effort and on the other hand delivers the scatter information necessary and sufficient for scatter correction.

Experience shows that the dependencies of most parameters are constant and relatively soft. In this case SBF calculation is sufficient for just a few values of an individual parameter, interpolation can be used for intermediate values. In most cases a very good accuracy is achieved with three parameter values and cubic interpolation for intermediate values. But for example even with 5 independent parameters $3^5$=243 variants are already produced. This multiplicity can be reduced if the dependency of a specific parameter can be described by simple recalculations which can be derived for example from geometrical relationships or a produced by deviations of minimized curve adaptation. This applies for example to the dependency of the parameters SID, air gap, field size and filter thickness.

The SBFs 25 are most strongly dependent on the ray configuration in the object model, meaning on the overall path length 36 of the ray in the material and of the occupation of the path length 36 by bone tissue 27 and soft tissue 14 which the ray penetrates and in which the scatter processes also occur. It is noticeable here that the scatter distribution on the detector 11 is essentially determined by scatter processes in a exit layer of the scatter body near to its surface. The thickness of this effective exit layer corresponds to around 1-2 average scatter path lengths. One average scatter path length is the reciprocal value of the linear attenuation coefficient. For water-like material and an energy of 70 keV this is typically about 5 cm.

Thus a discrimination of the ray configurations with a mesh width of around 5 cm is recommended. The ray length rayleng of the ray in the object (i.e. the object thickness) is varied for example in the range 5 to 40 cm in steps of 5 cm. Each fixed ray length rayleng is subdivided into a number ksub of subsections (for example of 5 cm length or coarser in their turn). Finally for each subsection different pairs of "mass occupancies"=length*density for bone tissue bK and soft tissue bW are varied. For example the range of values which occurs can essentially be covered with the combination bK=0, 4, 8 g/cm$^2$ and bW=0, 2.5, 5 g/cm$^2$, in relation to 5 cm material thickness. To reduce the number of variations one can example discretize the exit of the ray from the object near to the detector with one or two subsections of length 5 cm, but group the remaining ray length far away from the detector into a single subsection.

Overall the number of different SBFs 25 to be calculated by means of Monte Carlo simulation can be restricted to several hundred up to a maximum of several thousand taking into account the measures stated. The SBF atlas obtained in this way can be expanded by interpolation of the SBFs 25 for a finer parameter discretization. One SBF 25 stored in the SBF atlas represents one scatter category in this case.

If the computer tomography device 1 is operated both without and also with an anti-scatter grid, then the Monte Carlo calculations are to be made for both cases. Since the x-ray scatter is already reduced by the grid to about ⅕ it may be possible to work for simulation calculations with grids with a coarser parameter discretization.

The Monte-Carlo calculations for creating the SBF atlas need only be performed once for a production series of the same type of computer tomograph, for example with the same design of x-ray tube, the same detector, similar recording geometry or the same anti-scatter grid.

The propagation of the x-ray photons as a random process is known to be simulated with the Monte Carlo method.

Thus the results are affected by statistical fluctuations, depending on the method, these being smaller the greater the number of trajectories of x-ray photons which were calculated in the simulation. Without having to increase the computation time, the fluctuations can be reduced by suitable averaging of the calculated SBF if for theoretical reasons the SBF must exhibit symmetry characteristics, for example rotation symmetry in the case of a lack of anti-scatter grid or asymmetry in relation to two orthogonal axes when an anti-scatter grid is present). Finally the remaining rough estimates resulting from the Monte-Carlo calculation in the calculated SBFs 25 can be sufficiently eliminated by deviations of minimizing curve adaptation. By exploiting symmetries the memory space requirement for the SBFs 25 in the proposed SBF atlas can also be significantly reduced.

The above versions were designed to demonstrate the basic feasibility of the calculation and storage of an SBF atlas with currently available workstation computers:

The computing time requirements can be of the order of magnitude of weeks here, but can be significantly reduced by distributing it to a number of computers or by using more powerful computing systems with many fast processors. On the other hand the use of greater computing power can also be employed to calculate a larger number of ray configurations with finer parameter discretization or lateral inhomogeneous ray configurations as will be explained in embodiment 4.

Experimental Tuning

Equation (Eq. 6) shows the two-dimensional x-ray scatter distribution in the detector plane as a location-dependent generalized folding of the primary radiation distribution with location-dependent SBFs 25. It is expedient, for simple phantoms to determine the corresponding primary and x-ray scatter distribution through measurements and to compare them with the results of the calculations in accordance with (Eq. 6). Deviations can be largely reduced by better adapting of the Monte Carlo simulation an the real recording geometry and the physical radiation parameters and if necessary for example by corrective scaling factors. It is however to be noted that determining x-ray scatter distribution on a radiography system using measurements is relatively inaccurate. A typical imprecision of some 5% in the determination of the control component (scatter fraction=scatter intensity/total intensity) is to be reckoned with.

Disk-shaped and cylindrical phantoms with different thicknesses or diameters made of water or plastics with physical properties similar to water (for example polyethylene or Plexiglass), are suitable. The beam stop method has proven itself in particular for measuring x-ray scatter.

The major components of the correction method described here are as follows:
(1) the adaptive calculation of x-ray scatter distribution from an already reconstructed object volume in an efficient manner.
(2) the use of (inhomogeneous) Scatter-Beam-spread-Functions (SBF) which have already been calculated in advance and which thus only need to be accessed, saving on computing time, in the form of a large table (SBF atlas);
(3) covering essentially all recording parameters occurring (spectrum, air gap, SID, grid, etc.) and object parameters (combination of bone and soft tissue and further parameters) in the SBF atlas.
(4) a further feature of the method described is, that within the framework of segmented reprojection direct coupling with a hardening correction is produced almost automatically since the individual categories of scatter materials, for example bone tissue 27 and soft tissue 28 can be assigned the known actual attenuation coefficients.

EMBODIMENTS

The x-ray scatter correction described here can be employed with the following computer tomography devices (CT):CT with multi-row detector, CT with flat-panel detector (=FPD), angiography CT with C-arm and x-ray image amplifier or FPD, mobile C-arm CT with x-ray image amplifier or FPD.

Embodiment 0

We will refer to the basic x-ray scatter correction method already described in detail as embodiment 0.

Figure 5:
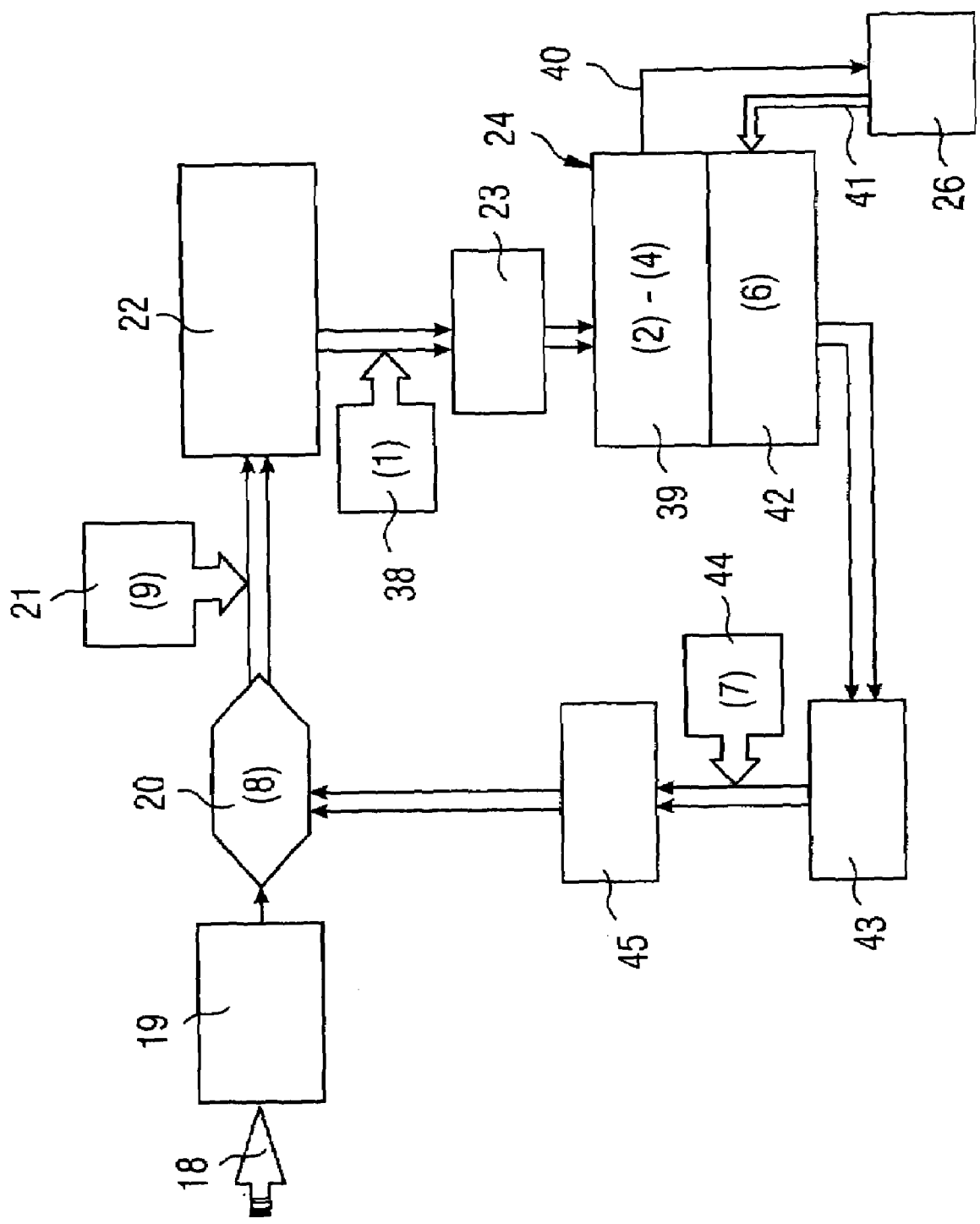
FIG. 5 a more detailed diagram of an embodiment of scatter correction.

Embodiment 0 is shown again in detail in FIG. 5. Data recording 18 leads to projection images 19 to which scatter correction 20 will be applied. An image reconstruction 21 produces a volume image 22. The volume image 22 is subjected to a coarsening 38 which leads to a scatter model 23. The coarsening 38 corresponds to the processing step (1) in which the number of voxels 31 and of detector pixels 32 has been decimated. The coarsening 38 leads to the scatter model 23 on the basis of which the scatter data calculation can be performed. A first processing section 39 comprises the processing steps (2) to (4) described above and leads to a lookup 40 in the SBF atlas stored in data memory 26. The SBFs 25 of the scatter data calculation 24 stored in the SBF atlas are made available by reading them out 41. If necessary interpolation is performed between the stored SBFs 25. In a second processing section 42 the processing steps (6) to (8) can then be performed. The lookup 40 and read out 41 correspond to the processing step (5) described above.

After the completion of scatter data calculation 24 scatter data 43 is present at low resolution. By a subsequent refinement 44, this can be converted in scatter data 45 of higher resolution. Details of the refinement 44 are described in connection with processing step (7).

Finally the scatter correction 20 in accordance with processing step (8) is performed and an image is reconstructed again 21 in accordance with processing step (9). The latter produces a scatter-corrected volume image 22. If necessary a new scatter model 23 can be derived from the scatter-corrected volume image 22 and the scatter correction 24 as well as the subsequent procedural steps including the scatter correction 20 can be performed again until a sufficient accuracy has been obtained for the volume image 22.

In order to efficiently reduce the computing effort, the fact that the x-ray scatter and its effect on the reconstructed CBCT volume is relatively smooth can be further exploited.

Embodiment 1

First the CBCT reconstruction is performed on the original possibly fine voxel- and detector pixel grid and for all projection directions.

The x-ray scatter is then corrected in accordance with embodiment 0 up to and including processing step (8a), with the transition to the original fine pixel grid having been completed in step (7).

The volume reconstruction in the processing step(9) however, unlike in embodiment 0, is only performed with a small number of projections. The number of projections can for example be reduced by a factor of 4. A greater reduction factor may also possibly be permitted. If the reconstruction of the uncorrected projection data with the reduced number is also available, an x-ray scatter correction volume is produced from the difference between corrected and uncorrected volume.

Finally this x-ray scatter correction volume is added to the reconstructed (uncorrected) object volume originally corrected with the full projection number. The result is the x-ray scatter corrected object volume.

Embodiment 2

In embodiment 1 (in the 3rd paragraph) the separate reconstruction of the uncorrected data with a reduced number of projections can be avoided by exploiting the linearity of the reconstruction: Only the uncorrected projection data needed is extracted, the difference to the x-ray scatter corrected projection data formed and the volume reconstruction only performed with the difference data. The result is equivalent to the x-ray scatter correction volume given above.

Embodiment 3

Figure 6:
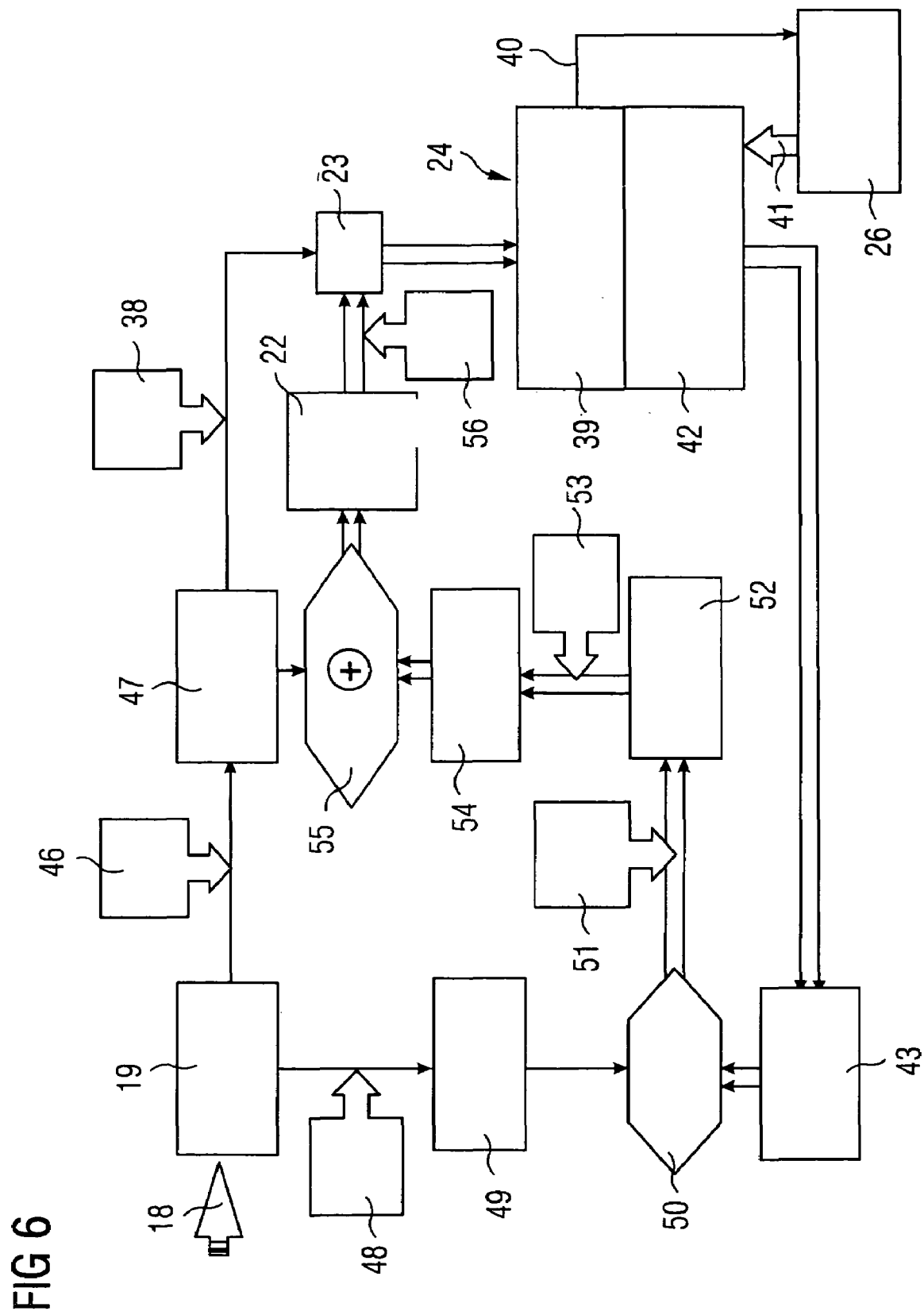
FIG. 6 a more detailed diagram of the execution sequence of a further embodiment of scatter correction.

Furthermore a third embodiment will be described in detail with reference to FIG. 6. The data recording 18 creates projection images 19 which are subjected to a high-resolution image reconstruction 46 which leads to a high-resolution uncorrected volume image 47. The high-resolution uncorrected volume image 47 is subjected to the coarsening 38 and thereby converted into the scatter model 23. Based on the scatter model 23 processing sections 39 and 42 can be performed. Finally scatter data 43 at low resolution is produced.

The projection images 19 are further subjected to a coarsening 48 which leads to projection images 49 with low local resolution. On the basis of the projection images 49 with low resolution a scatter correction 50 is undertaken, as well as a subsequent image reconstruction 51, with the image reconstruction 51 calculating a correction volume image 52 at low resolution. The correction volume image 52 is thus based, as in embodiment 2, on the difference between the uncorrected projection images 49 on the basis of the scatter data 43 corrected projection images. A subsequent refinement 53 produces a high-resolution correction volume image 54, which will be processed in an addition procedure 55 together with the high-resolution uncorrected volume image 47 into volume image 22. The corrected volume image 22 can then be subjected to a coarsening 56 in order to create a corrected scatter model 23 which can serve as the basis for a new execution of the correction cycle shown in FIG. 6 by double arrows. An advantage of the third embodiment shown in FIG. 6 is that the scatter correction can be largely performed at low resolution. This reduces the computing effort significantly.

Further simplifications can be achieved in that for example instead of the different location-dependent x-ray scatter spreading functions, a single typed x-ray scatter spreading function can be used. Processing step (6) is then reduce d to one folding which can be inverted with the aid of a Fourier transformation. In this case the iterative calculation undertaken in processing step (8) can be replaced by a deconvolution.

Embodiment 4

Finally a fourth embodiment will be explained. This differs from the embodiments previously described in that a further differentiation of the ray configurations or scatter categories is provided.

In particular the parameterization of the x-ray scatter spread functions (SBFs) 25 is further differentiated in that subsections 37, into which the ray length 36 is subdivided, cannot just continue homogeneously, as is shown in FIG. 4, but also inhomogeneously in a lateral spread direction at right angles to the direction of spread. Account should be taken here however of the fact that inhomogenities at a lateral distance of more than around two ray lengths have practically no influence. On the other hand the scatter material can be "smeared" over the width of around one ray length (typically around 5 cm) in each case. Taking account of laterally inhomogeneous SBFs can above all play a part in the vicinity of the object edge where on one side no further scatter material adjoins.

Taking account of laterally inhomogeneous SBFs required a significant enlargement of the multiplicity and demands significantly greater computing power and computing time for creation of the SBF atlas.

A common factor to all embodiments is that the calculation of the SBFs 25 with the aid of Monte Carlo simulations allows detailed modeling of the physical reality. Multiple scatter processes along the path of an x-ray photon and the effects of complex surfaces can especially be modeled.

Further the concept of x-ray scatter correction described here allows an object-specific correction of the x-ray scatter to be performed. To clarify the meaning of a correction of the x-ray scatter tuned to the material composition of the object to be examined, reference will be made to FIGS. 7 to 9, in which the results of the simulation calculations are presented.

Figure 7:
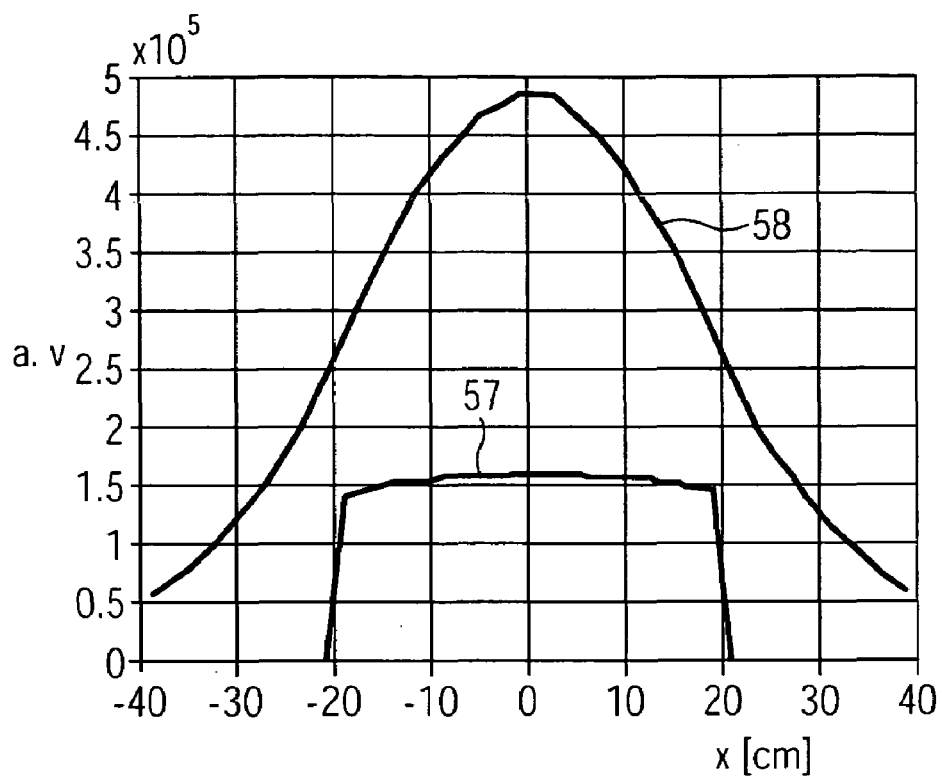
FIG. 7 a diagram in which the distribution of the primary radiation and the secondary radiation is shown for a specific object model.

FIG. 7 shows a primary radiation distribution 57 and a secondary radiation distribution 58 along the central detector row of a 30×40 cm$^2$ flat-panel detector.

The two distributions are each entered in arbitrary units along the x-coordinate.

It has been assumed for the simulation that the pixels of the flat image detector each have an extent of 1×1 cm$^2$. It has further been assumed that the flat image detector involved is a flat image detector with CsI-scintillator. The flat image detector should also no be assigned to any anti-scatter grid for echo suppression of the x-ray scatter.

The x-ray tube is assumed to have a tungsten anode and of an x-ray voltage of 70 kV. The radiation emitted by the x-ray tube has been collimated to the full detector surface on the tube side.

The gap between x-ray source and flat image detector was selected as 115 cm and the air gap between scatter body and the flat image detector as 20 cm.

A plate-shaped spread-out scatter body was used for the simulation, in which in the ray direction 5 cm of bone preceded 20 cm of water. Typical value were used for the specification of the bones. Density 1,486 g/cm$^3$, atomic proportions H: 7; O: 3.06; C: 1.92; N: 0.28; P:0.22; Ca.: 0.25.

Overall the path of 2×10$^9$ photons was simulated.

The primary radiation distribution 57 and the secondary radiation distribution 58 correspond to the energy values deposited in the middle detector row extending along the lengthwise side in arbitrary units.

Figure 8:
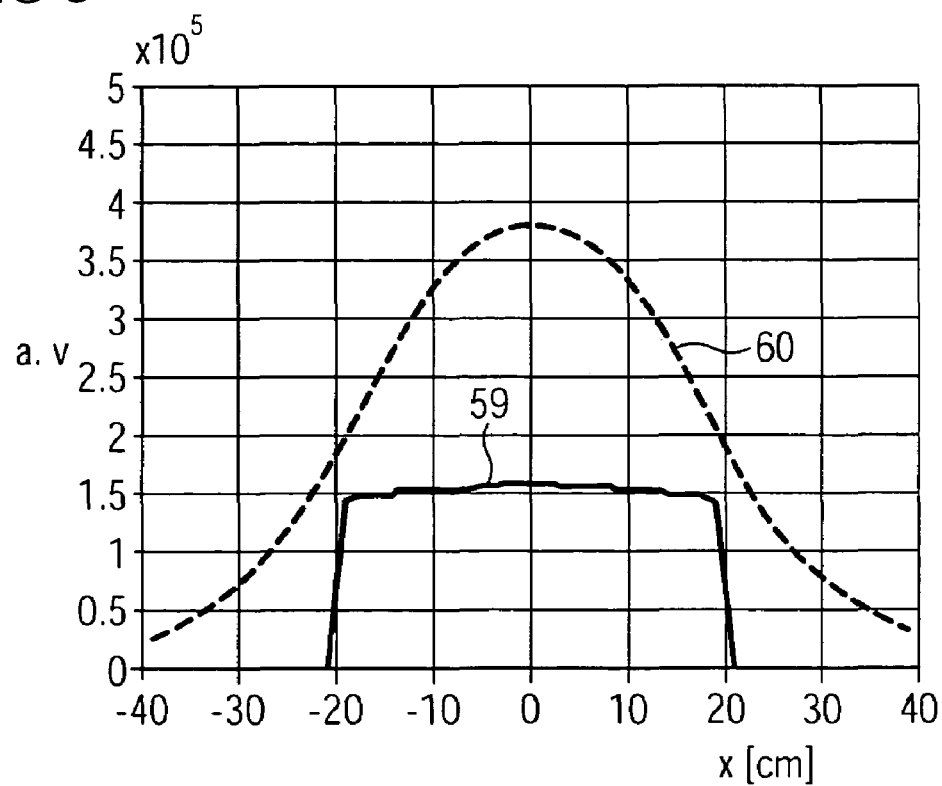
FIG. 8 a diagram in which the distribution of the primary radiation and the secondary radiation is shown for an object model with material distribution which can be inverted by comparison with FIG. 7.

The same conditions also used for the computation of the primary radiation distribution 59 and the secondary radiation distribution 60 shown in FIG. 8. However the sequence of bone and water was reversed. For the simulations based on the primary radiation distribution 59 and the secondary radiation distribution 60 a plate-shaped scatter body has been assumed in which the 5 cm bone lies behind 20 cm water in the radiation direction.

A comparison of the diagrams in the FIGS. 7 and 8 shows clearly that the primary radiation distributions 57 and 59 are essentially the same. The secondary radiation distributions 58 and 60 by contrast differ widely from each other. In particular the intensity of the secondary radiation distribution 58 in the middle of the detector plane is up to 27% greater than that of the secondary radiation distribution 60.

These differences become even greater if a greater density or layer density is used for the bone.

Figure 9:
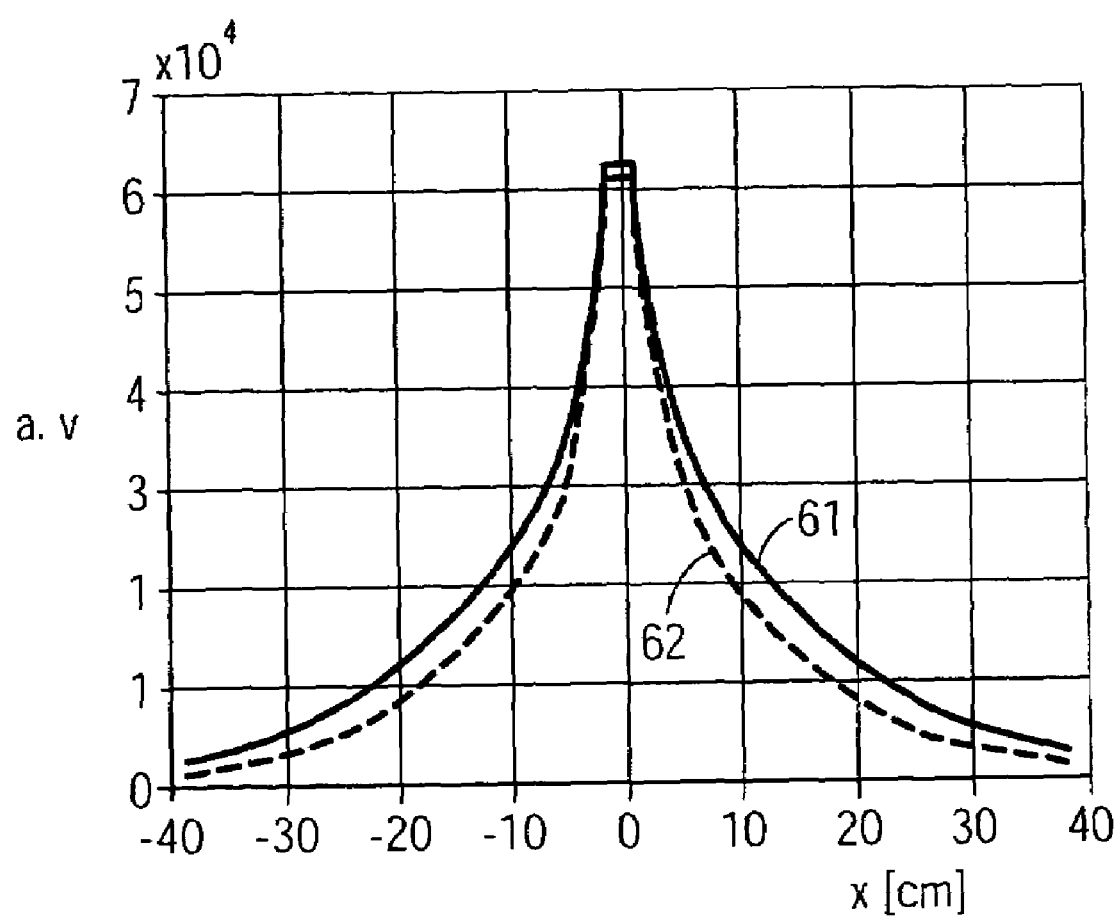
FIG. 9 a diagram in which x-ray scatter distribution functions are shown for different material compositions of an object to be examined.

Finally FIG. 9 shows x-ray scatter spread functions 61 and 62. X-ray scatter spread functions 61 and 62 were calculated by assuming a collimation of the x-ray radiation on an individual pixel with a spread of 1×1 cm$^2$.

The x-ray scatter spread functions 61 reflect the case in which a 5 cm layer of bone is located before a 20 cm layer of water in the radiation direction, and x-ray scatter spread function 62 reflects the case in which 5 cm bone lies behind 20 cm water in the radiation direction.

FIGS. 7 to 9 clearly shown that in the energy range between around 60 and 150 keV, in which operations are undertaken in standard computer tomography, a pre-constructive correction of the x-ray scatter is not sufficient. This is because this type of correction would have to use the attenuation of the primary radiation as its starting point. This would however lead in the energy range of interest to unsatisfactory results. This is because the examples in FIGS. 7 and 8 T show, that with the same attenuation of the primary radiation the distribution of the secondary radiation can turn out differently depending on the properties of the material.

With the post-reconstructive approach described here on the other hand the x-ray scatter can be satisfactorily corrected, since the calculation of the x-ray scatter correction can take account of the distribution of material in the object to be examined.

The invention claimed is:

1. A computer tomography device, comprising:
   a radiographic source;
   a detector; and
   an evaluation unit connected to and arranged downstream of the detector for determining scatter information using a plurality of projection images provided by the detector, the projection images recorded relative to different projection directions, the evaluation unit configured to correct an x-ray scatter component present in the projection images using the scatter information, wherein the evaluation unit is further configured to:
   determine a three-dimensional object model based on the projection images,
   differentiate the object model according to a plurality of different scatter properties,
   read out pre-determined scatter information from a data memory based on the object model, wherein the scatter information are pre-determined using a Monte-Carlo-Simulation including interactions of photons with the object model and are stored in the data memory,
   determine a proportion of the x-ray scatter component present in an image area of a projection image by calculating and summing up x-ray scatter contributions related to further image areas surrounding the image area, and
   determine a distribution of the unscattered primary radiation by solving the implicit equation P+S(P)=T, where P is the distribution of the unscattered primary radiation, S(P) is the distribution of the x-ray scatter component depending on the unscattered primary radiation and T is an overall x-ray scatter distribution present in the projection images.

2. The device in accordance with claim 1, wherein the scatter information include scatter distributions representing a radiation distribution caused by scattering of a radiation emitted by the radiographic source and directed to a specific area of the detector, the radiation distribution including information of such parts of the radiation directed to the specific area of the detector but received by further areas of the detector adjacent to the specific area.

3. The device in accordance with claim 1, wherein the scatter distributions are scaled relative to an intensity of unscattered primary radiation received by the detector.

4. The device in accordance with claim 1, wherein the object model is determined using computer-tomographic specific reconstruction and re-projection algorithms.

5. The device in accordance with claim 1, wherein the x-ray scatter component is corrected including coarsening the object model relative to a spatial resolution of the object model.

6. The device in accordance with claim 1, wherein the object model includes a plurality of object model segments related to a plurality of scatter categories.

7. The device in accordance with claim 1, wherein the evaluation unit is further configured to:
   determine a low resolution uncorrected and corrected volume images, the low resolution uncorrected and corrected volume images based on a plurality of scatter-corrected and non-scatter-corrected coarsened projection images,
   determine a correction volume image based on a difference between the low resolution uncorrected and corrected volume images, and
   correct a high resolution uncorrected volume image based on the correction volume image, the high resolution uncorrected volume image being reconstructed from the projection images provided by the detector that are non-coarsened.

8. The device in accordance with claim 1, wherein the evaluation unit is further configured to:
   determine a correction volume image based on a difference between a plurality of scatter-corrected and non-scatter-corrected projection images, and
   correct an uncorrected volume image based on the correction volume image, the uncorrected volume image being reconstructed from the projection images provided by the detector.

9. The device in accordance with claim 1, wherein the evaluation unit is further configured to correct the x-ray scatter component using an iteration process based on a scatter-corrected volume image.

10. A method for correcting a x-ray scatter component present in projection images recorded by a computer tomograph, comprising:
    recording a plurality of projection images related to an object to be examined by a computer tomograph having a radiographic source, a detector, and an evaluation unit connected to the detector and arranged downstream of the detector, the plurality of projection images recorded relative to different projection directions;
    determining a three-dimensional object model from the projection images;

differentiating the object model according to a plurality of different scatter properties of the object to be examined;
correcting the x-ray scatter component using pre-determined scatter information, wherein the pre-determined scatter information are scatter beam spread functions and:
　calculated using a Monte-Carlo-Simulation including interactions of photons with the object to be examined,
　stored in a data memory,
　retrieved from the data memory based on the differentiate object model;
determining a proportion of the x-ray scatter component present in an image area of a projection image by calculating and summing up x-ray scatter contributions related to further image areas surrounding the image area;
determining a distribution of the unscattered primary radiation by solving the implicit equation $P+S(P)=T$, where P is the distribution of the unscattered primary radiation, S(P) is the distribution of the x-ray scatter component depending on the unscattered primary radiation and T is an overall x-ray scatter distribution present in the projection images; and
medically examining the object using the corrected projection images.

* * * * *